United States Patent
McConnell et al.

(10) Patent No.: US 11,491,171 B2
(45) Date of Patent: *Nov. 8, 2022

(54) SYNTHETIC COMPOSITION AND METHOD FOR MODULATING EMOTION AND MOOD DISORDERS

(71) Applicant: GLYCOM A/S, Hørsholm (DK)

(72) Inventors: Bruce McConnell, La Tour de Peilz (CH); Emma Elison, Hjärup (SE); Louise Kristine Vigsnæs, Copenhagen (DK)

(73) Assignee: GLYCOM A/S, Hørsholm (DK)

( * ) Notice: Subject to any disclaimer, the term of this patent is extended or adjusted under 35 U.S.C. 154(b) by 68 days.

This patent is subject to a terminal disclaimer.

(21) Appl. No.: 17/026,616

(22) Filed: Sep. 21, 2020

(65) Prior Publication Data
US 2021/0000849 A1 Jan. 7, 2021

Related U.S. Application Data

(63) Continuation of application No. 15/771,652, filed as application No. PCT/DK2016/050345 on Oct. 28, 2016, now Pat. No. 10,780,103.

(30) Foreign Application Priority Data

Oct. 28, 2015 (DK) .............. PA 2015 70697
Feb. 24, 2016 (DK) .............. PA 2016 70101

(51) Int. Cl.
| A61K 31/702 | (2006.01) |
| A23L 33/00 | (2016.01) |
| A23L 33/15 | (2016.01) |
| A61P 25/22 | (2006.01) |
| A61P 25/24 | (2006.01) |

(52) U.S. Cl.
CPC ............ *A61K 31/702* (2013.01); *A23L 33/15* (2016.08); *A23L 33/30* (2016.08); *A61P 25/22* (2018.01); *A61P 25/24* (2018.01); *A23V 2002/00* (2013.01)

(58) Field of Classification Search
CPC ........ A61K 31/702; A23L 33/30; A23L 33/15
See application file for complete search history.

(56) References Cited

U.S. PATENT DOCUMENTS

| 10,780,103 B2 * | 9/2020 | McConnell ............ A23L 33/30 |
| 2012/0171166 A1 | 7/2012 | Chow et al. |
| 2012/0208782 A1 | 8/2012 | Frantz |
| 2015/0265661 A1 | 9/2015 | Newburg et al. |
| 2015/0305384 A1 | 10/2015 | Chichlowski et al. |
| 2015/0320778 A1 * | 11/2015 | Chow .................... A23C 9/206 514/61 |
| 2016/0243139 A1 | 8/2016 | Vigsnæs et al. |
| 2016/0287637 A1 | 10/2016 | McConnell et al. |

FOREIGN PATENT DOCUMENTS

| EP | 2708145 A1 | 3/2014 |
| EP | 2708147 A1 | 3/2014 |
| EP | 2842560 A1 | 4/2015 |
| WO | 0104341 A1 | 1/2001 |
| WO | 2007101862 A1 | 9/2007 |
| WO | 2010115934 A1 | 10/2010 |
| WO | 2010115935 A1 | 10/2010 |
| WO | 2011023689 A1 | 3/2011 |
| WO | 2011100980 A1 | 8/2011 |
| WO | 2012007588 A9 | 1/2012 |
| WO | 2012089783 A1 | 7/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013032674 A1 | 3/2013 |
| WO | 2013044928 A1 | 4/2013 |
| WO | 2013091660 A1 | 6/2013 |
| WO | 2013139344 A1 | 9/2013 |
| WO | WO2014/043330 * | 3/2014 | .............. A23L 1/29 |
| WO | 2014100126 A1 | 6/2014 |
| WO | 2014100191 A1 | 6/2014 |
| WO | 2014164882 A1 | 10/2014 |
| WO | 2015157098 A1 | 10/2015 |
| WO | 2016066175 A1 | 5/2016 |

OTHER PUBLICATIONS

Barbara, G. et al., "Mast Cell-Dependent Excitation of Visceral-Nociceptive Sensory Neurons in Irritable Bowel Syndrome," Gastroenterology, 2007, vol. 132, pp. 26-37.
Bottacini, F. et al., "Diversity, ecology and intestinal function of bifidobacteria," Microbial Cell Factories, 2014, vol. 13, 15 pages.
Chen, X., "Human Milk Oligosaccharides (HMOS): Structure, Function, and Enzyme-Catalyzed Synthesis," Advances in Carbohydrate Chemistry and Biochemistry, 2015, vol. 72, pp. 113-190.
Collins, S.M. et al., "The Relationship Between Intestinal Microbiota and the Central Nervous System in Normal Gastrointestinal Function and Disease," Gastroenterology, 2009, vol. 136, pp. 2003-2014.
Dinan, T.G. et al., "Psychobiotics: A Novel Class of Psychotropic," Biol Psychiatry, 2013, vol. 74, pp. 720-726.
Duranti, S. et al., "Exploration of the Genomic Diversity and Core Genome of the Bifidobacterium adolescentis Phylogenetic Group by Means of a Polyphasic Approach," Applied and Environmental Microbiology, 2013, vol. 79(1), pp. 336-346.

(Continued)

*Primary Examiner* — Pancham Bakshi

(74) *Attorney, Agent, or Firm* — Neal, Gerber & Eisenberg LLP

(57) ABSTRACT

A synthetic composition for use in treating or improving one or more emotion and/or mood disorders in a patient, characterised in that the composition contains an effective amount of one or more neutral human milk oligosaccharides, is disclosed.

18 Claims, No Drawings

(56) References Cited

OTHER PUBLICATIONS

Ferrari, A.J. et al., "Burden of Depressive Disorders by Country, Sex, Age, and Year: Findings from the Global Burden of Disease Study 2010," PLOW Medicine, 2013, vol. 10(11), 12 pages.
Kendler, K.S. et al., "Illicit psychoactive substance use, abuse and dependence in a population-based sample of Norwegian twins," Psychol Med., 2016, vol. 36(7), pp. 955-962.
Kim, G. et al., "Methanobrevibacter smithii Is the Predominant Methanogen in Patients with Constipation-Predominant IBS and Methane on Breath," Dig Dis Sci, 2012, vol. 57, pp. 3213-3218.
Longstreth, G.F. et al., "Functional Bowel Disorders," Gastroenterology, 2006, vol. 130, pp. 1480-1491.
Qin, J. et al., "A human gut microbial gene catalogue established by metagenomic sequencing," Nature, 2010, vol. 464, pp. 59-65.
Savignac, H.M. et al., "Bifidobacteria exert strain-specific effects on stress-related behavior and physiology in BALB/c mice," Neurogastroenterol Motil, 2014, vol. 26, pp. 1615-1627.
Tarr, A.J. et al., "The prebiotics 3'Sialyllactose and 6'Sialyllactose diminish stressor-induced anxiety-like behavior and colonic microbiota alterations: evidence for effects on the gut-brain axis", Brain Behav Immun., 2015, vol. 50, pp. 166-177.
Urashima, T. et al. (2011) Nutrition and Diet Research Progress: Milk Oligosaccharides. New York: Nova Science Publishers, Inc. 92 pages.
International Search Report and Written Opinion dated Jan. 25, 2017 for International Application No. PCT/DK2016/050345, 17 pages.
O'Mahony, S.M., et al., "Serotonin, tryptophan metabolism and the brain-gut-microbiome axis," Behavioural Brain Research, 2015, vol. 277, pp. 32-48.

\* cited by examiner

SYNTHETIC COMPOSITION AND METHOD FOR MODULATING EMOTION AND MOOD DISORDERS

CROSS-REFERENCE TO RELATED APPLICATION

This is a continuation of U.S. patent application Ser. No. 15/771,652, filed Apr. 27, 2018, which is a national stage entry pursuant to 35 U.S.C. § 371 of International Patent Application No. PCT/DK2016/050345, filed on Oct. 28, 2016, which claims priority to Denmark Patent Application No. PA 2015 70697, filed Oct. 28, 2015, and Denmark Patent Application No. PA 2016 70101, filed Feb. 24, 2016, the contents of all of which are fully incorporated herein by reference.

FIELD OF THE INVENTION

This invention relates generally to compositions and methods for the treatment of emotion and mood disorders, for example anxiety and depression.

BACKGROUND TO THE INVENTION

Anxiety disorders are a group of mental disorders characterised by feelings of anxiety and fear (*Diagnostic and Statistical Manual of Mental Disorders*, American Psychiatric Association, 5th ed., 2013). Anxiety often occurs with other mental disorders, particularly mood or depressive disorders. Medication options are benzodiazepines which are used for the short-term relief of severe anxiety, antidepressants, and beta-blockers to reduce some of physical symptoms, such as rapid heartbeats and shaking.

Mood or depressive disorders are a group of disorders involving primary disturbances of mood. These include depression, major depressive disorder (MDD or clinical depression), dysthymia, and bipolar disorder. Patients suffering from depression exhibit feelings of sadness, low mood and an aversion to activity and this mood can affect a person's thoughts, behaviour, feelings and sense of well-being. A depressed person may feel sad, anxious, empty, hopeless, worried, helpless, worthless, guilty, irritable, hurt or restless.

Major depressive disorder (MDD) is a disabling, severe mental disorder characterised by episodes of all-encompassing low mood, low self-esteem and loss of interest or pleasure in normally enjoyable activities. The illness tends to be chronic and repeated episodes are common. Other symptoms of MDD may include irritability or frustration, sleep disturbances, tiredness and lack of energy, changes in appetite, anxiety, agitation, restlessness, feelings of worthlessness or guilt, trouble thinking and concentrating, and unexplained physical problems, such as back pain or headaches. The disorder is a significant contributor to the global burden of disease and affects people in all communities across the world (Ferrari et al. *PLoS Med.* 10, e1001547 (2013)). MDD is a highly prevalent psychiatric disorder with twin studies revealing that up to 40% of MDD cases are genetically determined (Kendler et al. *Psychol. Med.* 36, 955, (2006)).

Although the exact causes of mood disorders are unknown, it is believed that a variety of factors may be involved, such as brain chemistry and physical brain differences, hormones, inherited traits and life events. This lack of knowledge of causation has made treatment difficult.

Many types of antidepressant medications are available to treat mood disorders that present with depression. Some available drugs include selective serotonin reuptake inhibitors (SSRIs), serotonin and norepinephrine reuptake inhibitors (SNRIs), norepinephrine and dopamine reuptake inhibitors (NDRIs), tricyclic antidepressants, monoamine oxidase inhibitors (MAOIs), and atypical antidepressants such as vortioxetine. However, despite the availability of numerous treatment options, individual response to antidepressant medication is suboptimal and variable. That is, not all individuals respond equally to a given antidepressant and some do not respond at all. As many as one half of patients do not receive adequate treatment and many respond partially or not at all to treatment. The presence of residual symptoms is also associated with a higher risk of recurrence, more chronic depressive episodes and a shorter duration between episodes. Guidelines for treatment recommend four possible strategies for managing non-response or partial response including: increasing the dose of the antidepressant drug; replacing the drug with a different antidepressant drug; augmenting the antidepressant therapy with a non-antidepressant agent; or combining the initial antidepressant with a second antidepressant.

Despite the lack of general efficacy, all of the available drugs have side effects with many having serious side effects. Therefore safer, nutrition based option have also been investigated. One potential approach is the role of folate in central nervous system function because folate is a vitamin. Evidence suggests that folate can reduce depressive moods in certain patients; at least comparable to that of tricyclic antidepressants. Folate also appears to influence the rate of synthesis of tetrahydrobiopterin, a cofactor in the hydroxylation of phenylalanine and tryptophan, rate-limiting steps in the biosynthesis of dopamine, norepinephrine, and serotonin, neurotransmitters postulated to play a role in the pathogenesis of depression. In addition, methyltetrahydrofolate (MTHF) has been shown to bind to presynaptic glutamate receptors, where it may potentially modulate the release of other neurotransmitters, including the monoamines. However, folate appears to be best applicable to patients with certain genetic profiles (WO 2014/164882) and is probably not a solution for all patients.

Increasing evidence suggests that the intestinal microbiota also plays a key role in the generation of psychiatric disorders (Savignac et al. *Neurogastroenterol. Motil.* 26, 1615 (2014)). The intestinal microbiota consists of a vast bacterial community that resides primarily in the colon and lives in a symbiotic relationship with the host. The human gastrointestinal microbiota includes at least 1000 different species of bacteria, which collectively make up to $10^{14}$ bacterial cells, tenfold the number of human cells, and they encode 100-fold more unique genes than the human genome (Qin et al. *Nature* 464, 59 (2010)). A bidirectional neurohumoral communication system, known as the gut-brain axis, integrates the host gut and brain activities.

This has lead researchers to attempt using probiotics as a treatment option. Although data are limited, *Lactobacillus* and *Bifidobacterium* species have been shown to display potential therapeutic properties in psychiatric disorders (Dinan et al. *Biol. Psychiatry* 74, 720 (2013)). Also, early evidence indicates that some prebiotics may be another treatment option. The human milk oligosaccharides 3'-O-sialyllactose (3'-SL) and 6'-O-sialyllactose (6'-SL) support normal behavioural responses in mice during stressor exposure, potentially through effects on the gut microbiota-brain axis (Tarr et al. *Brain Behav. Immun.* 50, 166 (2015)).

Therefore there remains a need for a generally safe and effective way for treating emotion and mood disorders, such as anxiety and depression.

SUMMARY OF THE INVENTION

In one aspect, this invention relates to one or more neutral human milk oligosaccharides ("neutral HMOs") for use in treating emotion and/or mood disorders, for example anxiety and/or depression, particularly in a patient having one or more of stress, bacterial overgrowth, dysbiosis and an impaired mucosal barrier.

In another aspect, this invention provides a synthetic composition for use in treating emotion and/or mood disorders, for example anxiety and/or depression, particularly in a patient having one or more of stress, bacterial overgrowth, dysbiosis and an impaired mucosal barrier, characterised in that the composition contains an effective amount of one or more neutral HMOs. The synthetic composition is preferably a nutritional composition. The method can be an adjunct treatment for a patient receiving other medication.

In another aspect, this invention provides a method for treating an emotion and/or mood disorder in a patient, for example anxiety and/or depression in a patient, particularly a patient having one or more of stress, bacterial overgrowth, dysbiosis and an impaired mucosal barrier, the method comprising orally or enterally administering to the patient an effective amount of one or more neutral HMOs, preferably in the form of a synthetic composition. Preferably the abundance of bifidobacteria, more preferably a *Bifidobacterium* of the *B. adolescentis* phylogenetic group, especially *Bifidobacterium adolescentis* and/or *Bifidobacterium pseudocatenulatum*, is also increased in the colon of the patient with the neutral HMO therapy. Preferably one or more of bacterial overgrowth, dysbiosis and/or impairment of mucosal barrier, is also reduced in the patient.

In a further aspect, this invention provides a method for maintaining an emotion and/or mood disorder patient in remission, for example an anxiety and/or depression patient, particularly a patient having one or more of stress, bacterial overgrowth, dysbiosis and/or an impaired mucosal barrier, the method comprising orally administering to the patient an effective amount of one or more neutral HMOs, preferably in the form of a synthetic composition.

The patient can be administered a higher amount, preferably 5 g to 10 g per day, of the one or more neutral HMOs for an initial treatment period, followed by a lower amount, preferably 1 g to 5 g per day, for a maintenance period. The initial treatment period can be 1 to 12 weeks. The maintenance period is at least 6 months.

In a further aspect, this invention provides a use of one or more neutral HMOs, preferably in the form of a synthetic composition, for treating one or more, emotion and/or mood disorders, for example anxiety and/or depression, particularly a patient having one or more of stress, bacterial overgrowth, dysbiosis and an impaired mucosal barrier.

In all aspects, the neutral HMO is preferably selected from 2'-FL, 3-FL, DFL, LNT, LNnT and LNFP-I. More preferably the neutral HMO is a combination of one or more core HMOs and one or more fucosyl HMOs, for example 2'-FL and/or DFL and LNnT and/or LNT. The 2'-FL and/or DFL and LNnT and/or LNT may be present in a mass ratio of about 4:1 to 1:1; more preferably about 3:1 to 1:1.

DETAILED DESCRIPTION OF THE INVENTION

In accordance with this invention, it has been surprisingly found that neutral human milk oligosaccharides (neutral HMOs), advantageously 2'-FL, 3-FL, LNT, LNnT, LNFP-I and DFL, are able to treat emotion and/or mood disorders, for example anxiety and depression, particularly in patients who are suffering from stress, bacterial overgrowth, dysbiosis or an impaired mucosal barrier. It is believed that the neutral HMOs can: (1) act as prebiotics to promote beneficial bacteria growth, especially bifidobacteria, and reduce bacterial overgrowth and dysbiosis; (2) act as decoys for pathogens by binding to them and thereby reduce/prevent binding of the pathogens to epithelial cells in the gastrointestinal tract; (3) act to reduce chronic mucosal inflammation; and/or (4) repair damage to the mucosal barrier. By reducing chronic mucosal inflammation including reducing mast cell degranulation, and/or repairing damage to the mucosal barrier, the neutral HMOs can also have beneficial effects on the enteric nervous systems of patients; potentially reducing anxiety and stress. Further, bifidobacteria, including *Bifidobacterium adolescentis*, are able to synthesize folate de novo, ensuring its constant bioavailability, and can secrete neuromodulators such as gamma-aminobutyric acid (GABA), a potent inhibitory neurotransmitter involved in reducing stress, anxiety and depression.

The intestinal bacteria may directly communicate with the central nervous system by way of the vagal sensory nerve fibres and the peripheral immune system. By altering the microbiota to increase bifidobacteria abundance, amongst other impacts, neutral HMOs may be capable of influencing neurotransmission in the paraventricular hypothalamus, the central nucleus of the amygdala, and the bed nucleus of the stria terminalis. All three of these regions are involved in the processing of emotions related to anxiety and mood.

Neutral HMOs for treating emotion and/or mood disorders as disclosed above can preferably be one or more fucosylated HMOs, or one or more non-fucosylated HMOs. In one embodiment, the neutral HMO is a mixture of neutral HMOs, even preferably a mixture comprising or consisting of a fucosylated and a non-fucosylated neutral HMO. Particularly, the mixture contains or consists of a fucosylated neutral HMO selected from the list consisting of 2'-FL, 3-FL, DFL and LNFP-I, and a non-fucosylated neutral HMO selected from the list consisting of LNT and LNnT. In one preferred embodiment, the mixture comprises or consists of 2'-FL and LNnT.

Embodiments of the invention are described using general terms and definitions of the following paragraphs. Still, in some cases, a term may be defined in the context of a particular embodiment.

According to the invention the term "patient" designates a non-infant human individual diagnosed with IBS. The term "non-infant" means an individual of any age above 3 years, e.g. it can be a child, a teenager, an adult or an elderly.

In accordance with this invention, the term "oral administration" preferably means any conventional form for the oral delivery of a composition to a patient that causes the deposition of the composition in the gastrointestinal tract (including the stomach) of the patient. Accordingly, oral administration includes swallowing of composition by the patient, enteral feeding through a naso-gastric tube, and the like.

Also herein, the term "effective amount" preferably means an amount of a composition that provides a neutral human milk oligosaccharide in a sufficient amount to render a desired treatment outcome in a patient. An effective amount can be administered in one or more doses to the patient to achieve the desired treatment outcome.

Also herein, the term "mood disorder" preferably means a mental disorder involving a primary disturbance of a mood resulting in the mood being distorted or inconsistent with circumstances. Mood disorders include depression, major depressive disorder, dysthymia and bipolar disorder.

Also herein, the term "emotional disorder" means a mental disorder involving a primary disturbance of emotions resulting in the emotions being distorted or inconsistent with circumstances. Emotional disorders include excessive anxiety, fear, anger, happiness, etc.

Also herein, the term "neutral human milk oligosaccharide" or "neutral HMO" preferably means a complex carbohydrate found in human breast milk that is in neutral form (not acidic form). More than about 200 different HMO structures are known to exist in human breast milk (Urashima et al. *Milk Oligosaccharides*, Nova Biomedical Books, New York, 2011; Chen *Adv. Carbohydr. Chem. Biochem.* 72, 113 (2015)). Neutral HMOs can be core and fucosylated oligosaccharides. Core HMOs are non-fucosylated neutral HMOs and consist of Glc, Gal and GlcNAc and are devoid of Fucose and sialic acid. Examples of core HMOs include lacto-N-tetraose (LNT), lacto-N-neotetraose (LNnT), lacto-N-neohexaose (LNH), lacto-N-hexaose (LNH) and para-lacto-N-neohexaose (pLNnH). Fucosyl HMOs are fucosylated lactoses or fucosylated core HMOs such as 2'-fucosyllactose (2'-FL), lacto-N-fucopentaose I (LNFP-I), lacto-N-difucohexaose I (LNDFH-1), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH).

Also herein, the terms "microbiota", "microflora" and "microbiome" preferably mean a community of living microorganisms that typically inhabits a human's, particularly an adult's, bodily organ(s) or part(s). The most dominant members of the gastrointestinal microbiota include microorganisms of the phyla of *Firmicutes, Bacteroidetes, Actinobacteria, Proteobacteria, Synergistetes, Verrucomicrobia, Fusobacteria,* and *Euryarchaeota*. At genus level the dominant microorganisms are *Bacteroides, Faecalibacterium, Bifidobacterium, Roseburia, Alistipes, Collinsella, Blautia, Coprococcus, Ruminococcus, Eubacterium* and *Dorea*; and at species level common species are *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. In some instances, the gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

Also herein, the term "*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)).

The neutral HMOs can be isolated or enriched by well-known processes from milk(s) secreted by mammals including, but not limited to human, bovine, ovine, porcine, or caprine species. The neutral HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, and mixtures of human milk oligosaccharides can be made as described in WO 2012/113405. As examples of enzymatic production, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 describes how to make core human milk oligosaccharides optionally substituted by fucose using genetically modified *E. coli*. If it is desired to additionally include acidic HMOs, these can be obtained as described in WO 2012/113404, WO 2012/007588, WO 01/04341 and WO 2007/101862.

The synthetic composition comprising one or more neutral human milk oligosaccharides can take any suitable form. The term "synthetic composition" designates a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. For example, the composition can be in the form of a nutritional composition which contains other macronutrients such as proteins, lipids or other carbohydrates. The synthetic composition can also be an incomplete nutritional composition in unit dosage form or pharmaceutical composition. In one embodiment, the synthetic compositions contain one or more core HMOs and one or more fucosyl HMOs. In a preferred embodiment, the synthetic composition contains 2'-FL and/or DFL, and LNnT and/or LNT.

Nutritional Compositions

A nutritional composition can contain sources of protein, lipids and/or digestible carbohydrates and can be in powdered or liquid forms. The composition can be designed to be the sole source of nutrition or a nutritional supplement. For emotion or mood disorder patients, a nutritional supplement is preferred; especially a supplement which can form a meal or snack replacement. Preferably the nutritional composition is lactose-reduced or, better yet, lactose-free.

Suitable protein sources include milk proteins, soy protein, rice protein, pea protein and oat protein, or mixtures thereof. Milk proteins can be in the form of milk protein concentrates, whey protein or casein, or mixtures of both. Soy, rice, pea and oat protein can be in the form or protein isolated. The protein can be whole protein or hydrolysed protein, either partially hydrolysed or extensively hydrolysed. The protein can provide about 5% to about 50%, preferably about 10% to 30%, of the energy of the nutritional composition. The protein source preferably is not a source of carbohydrates such as lactose. Therefore, if a milk protein is used as the protein source, the milk protein is preferably lactose-reduced or lactose-free.

Suitable digestible carbohydrates include maltodextrin, hydrolysed or modified starch or corn starch, glucose polymers, corn syrup, corn syrup solids, tapioca, sucrose, and glucose, or mixtures thereof. Generally digestible carbohydrates provide about 35% to about 75%, preferably about 45% to 70%, of the energy of the nutritional composition. Preferably the digestible carbohydrate is free from lactose.

Suitable lipids include rapeseed oil, sunflower seed oil, palm oil, soy oil, milk fat, corn oil and soy lecithin. Long-chain poly unsaturated fatty acids (LC-PUFA), especially omega-3 fatty acids such as docosahexaenoic acid (DHA), can be included in the lipid source because they have anti-inflammatory properties. Suitable sources of LC-PUFA are plant oils, marine plankton oils, fungal oils, and fish oils. The lipid source can also include medium chain triglycerides (MCT). Fractionated coconut oils are a suitable source of medium chain triglycerides. The lipid source preferably provides about 5% to about 25% of the energy of the nutritional composition; for example about 10% to 20%.

The nutritional composition preferably also includes vitamins and minerals. If the nutritional composition is intended to be a sole source of nutrition, it preferably includes a complete vitamin and mineral profile. Examples of vitamins include Vitamins A, B-complex (such as B1, B2, B6 and B12), C, D, E and K, niacin and acid vitamins such as pantothenic acid and folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition can also contain various other conventional ingredients such as preservatives, emulsifying agents, thickening agents, buffers, fibres and probiotics, especially probiotics which can help to reduce symptoms in patients (e.g. *Lactobacillus casei* strain Shirota, *B. infantis* 35624, *B. animal's* subsp. *lactis* BB-12, *B. lactis* Bi-07, *L. rhamnosus* GG, *L. rhamnosus* Lc705, *L. plantarum* DSM 9843, *L. plantarum* CECT7484, *L. plantarum* CECT7485, *L. acidophilus* NCFM, *L. fermentum* CECT5716, *B. breve* Bb99, *Propionibacterium freundenreichii* ssp. *Shermanii* JS, *P. acidilactici* CECET7483, *Streptococcus faecium*), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. Various flavours, fibres and other additives can also be present.

The nutritional composition can be prepared by any commonly used manufacturing techniques for preparing nutritional compositions in solid or liquid form. For example, the composition can be prepared from various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is also prepared by adding minerals, trace and ultra-trace minerals, thickening or suspending agents to water while heating and stirring. The resulting solution is held for 10 minutes with continued heat and agitation before adding carbohydrates (e.g. the neutral HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packaged to form an aseptically packaged nutritional composition. In this form, the nutritional composition can be in ready-to-feed or concentrated liquid form. Alternatively the composition can be spray dried and processed and packaged as a reconstitutable powder.

When the nutritional product is a ready-to-feed nutritional liquid, the total concentration of the one or more neutral HMOs in the liquid, by weight of the liquid, is from about 0.002% to about 3.0%, including from about 0.005% to about 2%, including from about 0.05% to about 1.0%. When the nutritional product is a concentrated nutritional liquid, the total concentration of HMOs in the liquid, by weight of the liquid, is from about 0.004% to about 6.0%, including from about 0.01% to about 4.0%, including from about 0.1% to about 2.0%.

Unit Dosage Forms

The synthetic composition of this invention can also be in a unit dosage form such as a capsule, tablet or sachet. For example, the composition can be formulated into single serve sachets containing the neutral HMOs, especially if higher doses are to be administered (more than 3 g). Alternative the composition can be in a tablet form comprising the human milk oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQlO") and glutathione.

The unit dosage forms, especially those in sachet form, can also include various nutrients including macronutrients.

Administration Dosing

For improving emotion and mood disorders in a patient, especially those suffering from stress, bacterial overgrowth, dysbiosis and/or an impaired mucosal barrier, the amount of neutral HMO(s) required to be administered to the patient will vary depending upon factors such as the risk and severity of the disease, the age of the patient, the form of the composition, and other medications being administered to the patient. However, the required amount can be readily determined by a medical practitioner and would generally be in the range of about 20 mg to about 30 g per day, preferably about 50 mg to about 20 g per day, or from about 100 mg to about 15 g per day, in certain embodiments from about 500 mg to about 10 g per day, preferably from about 1 g to about 7.5 g per day. During an initial treatment phase, the dosing can be higher, for example 100 mg to 30 g per day, preferably 500 mg to 15 g per day, more preferably 1 g to 10 g per day, in certain embodiments 2.5 g to 7.5 g per day. During a secondary prevention phase, the dosing can be reduced, for example, to 20 mg to 20 g per day, preferably 100 mg to 10 g per day, more preferably 500 g to 7.5 g per day, in certain embodiments 750 mg to 5 g per day.

EXAMPLES

Examples are now described to further illustrate the invention:

Example 1

Human Trial

A total of 40 male and female patients are recruited to participate in the study. The patients are screened from a pool of diagnosed patients with depression and anxiety. After a screening visit and run-in period of 1-2 weeks, the patients are selected. The patients are randomized into two groups, each of 20 patients, with one group consuming the treatment product and one group the placebo product for 8 weeks. The treatment product contains 5 grams of a combination of 2'-FL and LNnT while the control product contains 5 grams glucose. Both products are in powder form in a unit dosage container.

The patients are eligible to participate if they are aged 18-65, meet the formal diagnostic criteria for depression and anxiety, and suitable to complete a two month trial. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the initial visit (screening), each patient is given both written and oral information about the study and the patient is asked to sign an informed consent form. Patients are evaluated by a full review of clinical history. A blood sample for eligibility analysis is collected. A talk through of the electronic questionnaires (GSRS, QoL, BDI, BAI and BSFS) is performed to familiarise the patients with the electronic system, and equipment for faecal sampling is distributed to each patient. Patients are instructed to keep their samples in the freezer until the next visit.

At the second visit (beginning of intervention), eligibility criteria are checked and eligible subjects are randomised to the two arms in the trial. Symptoms (as measured by GSRS, QoL, BDI, BAI and BSFS scales) are assessed. Trial supplementation is distributed along with instructions on use of an electronic compliance diary. The faecal samples are collected and equipment for collecting new samples are distributed. Patients are reminded not to change their usual diet during the study.

Blood samples are collected for biomarker studies and biobanking. The serum from the blood samples is transferred to cryotubes and stored at −80° C. The following biomarkers are measured TNF-α, IL-1β, IL-8, IL-6, IL-12, IL-10, MIP-1β, hs-CRP, lipopolysaccharide binding protein, tryptase, antiflagellin, zonulin, histamine, prostaglandin 2, and cortisol. The faecal samples are stored at −80° C. until analysis. Microbiological analysis is performed on the faecal samples using the 16 S rRNA gene sequence.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSFS) information,
Gastrointestinal Symptom Rating Scale (GSRS) information. This questionnaire includes 15 items covering five dimensions (abdominal pain, indigestion, reflux, diarrhoea, constipation) and uses a seven-graded Likert scale,
Quality of life (QoL) information,
Beck Depression Inventory (BDI) and the Beck Anxiety Inventory (BAI) information.

4 weeks after commencement, there is an intermediate check. A physical examination is done and symptoms (as measured by GSRS, BSFS, QoL, BDI and BAI scales etc.) are reassessed. Faecal samples and blood samples are collected and analysed as before, and equipment for collection of new faecal samples are distributed.

At the end of the intervention (8 weeks), each patient has a visit with the medical team. A physical examination is done and symptoms (as measured by GSRS, BSFS, QoL, BDI and BAI scales etc.) are reassessed. Trial supplementation products are collected to check compliance.

Faecal samples and blood samples are collected and analysed as before.

Any patients who indicate any adverse events during the study are invited for a final visit to asked about any adverse events. This visit may be completed via telephone.

The treatment patients report a reduction in anxiety, a reduction in depression and an improvement in stress. The blood biomarker analysis indicates that the treatment patients have reduced levels of inflammatory markers, reduced gut permeability indicating an improved mucosal barrier, and reduced evidence of mast cell degranulation. The faecal analysis indicates that the treatment patients have reduced levels of bacterial overgrowth/dysbiosis and a higher level of bifidobacteria, especially a *Bifidobacterium* of the *B. adolescentis* phylogenetic group, preferably *Bifidobacterium adolescentis* and/or *Bifidobacterium pseudocatenulatum*.

Example 2

Nutritional Compositions

Ready to feed nutritional compositions are prepared from water, maltodextrin, corn syrup, sugar, milk protein concentrate, vegetable oil (canola, high oleic sunflower and corn), soy protein isolate, acacia gum, flavours, one or more neutral HMOs, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (Stevia), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The compositions each provide a nutritional supplement which is a good source of protein, low in fat, vitamins, minerals and antioxidants. Further, the compositions contain neutral HMOs which are able to promote the growth of beneficial intestinal bacteria, modulate chronic inflammation, improve mucosal barrier integrity and reduce anxiety and depression.

Example 3

Capsule Compositions

Capsule are each prepared by filling about 1 g of one or more neutral HMOs into a 000 gelatine capsule using a filing machine. The capsules are then closed. The neutral HMOs are in free flowing, powder form.

The invention claimed is:

1. A method for treating depression or anxiety in a patient, comprising orally administering to the patient an effective amount of a synthetic composition comprising one or more neutral human milk oligosaccharides (HMO), wherein the patient is administered 5 g to 10 g per day of the one or more neutral HMOs for an initial treatment period, followed by 1 g to 5 g per day of the one or more neutral HMOs, for a maintenance period, wherein the amount of the one or more neutral HMOs in the initial treatment period is greater than the amount of the one or more neutral HMOs in the maintenance period.

2. The method according to claim 1, wherein the method comprises treating anxiety.

3. The method according to claim 1, wherein the method comprises treating depression.

4. The method according to claim 1, wherein the neutral HMO is selected from the group consisting of 2'-fucosyllactose (2'-FL), 3-fucosyllactose (3-FL), difucosyllactose (DFL), lacto-N-tetraose (LNT) lacto-N-neotetraose (LNnT) and lacto-N-fucopentase I (LNFP-I).

5. The method according to claim 1, wherein the synthetic composition contains one or more neutral non-fucosylated HMOs and one or more neutral fucosyled HMOs.

6. The method according to claim 5, wherein the synthetic composition comprises 2'-FL and/or DFL, and LNnT and/or LNT.

7. The method according to claim 1, wherein the abundance of bifidobacteria, is increased in the patient.

8. The method of claim 1, wherein the patient further suffers from a condition selected from the group consisting of stress, bacterial overgrowth, dysbiosis and an impaired mucosal barrier.

9. The method according to claim 1, wherein the method comprises treating depression and anxiety.

10. The method according to claim 6 wherein the composition comprises 2'-FL and LNT.

11. The method according to claim 6 wherein the composition comprises 2'-FL and LNT, and DFL.

12. The method according to claim 1, wherein the patient further suffers from bacterial overgrowth.

13. The method according to claim 1, wherein the patient further suffers from dysbiosis.

14. The method according to claim 1, wherein the patient further suffers from an impaired mucosal barrier.

15. The method according to claim 1, wherein the composition is a nutritional composition further comprising folic acid.

16. The method of claim 7, wherein the bifidobacteria is *Bifidobacterium adolescentis, Bifidobacterium pseudocatenulatum*, or both.

17. The method of claim 6, wherein the mass ratio of 2'-FL and/or DFL to LNnT and/or LNT is about 4:1 to 1:1.

18. The method according to claim 1, wherein the initial treatment period is 1 to 12 weeks and the maintenance period is at least 6 months.

* * * * *